(12) United States Patent
Zoidis

(10) Patent No.: US 6,563,119 B1
(45) Date of Patent: May 13, 2003

(54) METHOD AND APPARATUS FOR IDENTIFICATION OF PLASTIC MATERIALS BY OPTICAL MEASUREMENTS

(75) Inventor: Evangelos Zoidis, Waiblingen (DE)

(73) Assignee: Sony International (Europe) GmbH, Berlin (DE)

( * ) Notice: Subject to any disclaimer, the term of this patent is extended or adjusted under 35 U.S.C. 154(b) by 9 days.

(21) Appl. No.: 09/626,609

(22) Filed: Jul. 27, 2000

(30) Foreign Application Priority Data

Jul. 29, 1999 (EP) .............................................. 99114883

(51) Int. Cl.$^7$ .............................. G01J 3/42; G01N 21/35
(52) U.S. Cl. ........................... 250/339.07; 250/339.06; 250/339.12
(58) Field of Search .................. 356/300, 320, 356/303, 939; 250/339.11, 341.1, 339.01, 339.07; 702/27, 28

(56) References Cited

U.S. PATENT DOCUMENTS

| 5,381,228 A | | 1/1995 | Brace |
| 5,435,309 A | | 7/1995 | Thomas |
| 5,773,502 A | * | 6/1998 | Takekoshi et al. .......... 524/411 |

FOREIGN PATENT DOCUMENTS

| EP | 0 559 305 | 9/1993 |
| EP | 0 607 048 | 7/1994 |

OTHER PUBLICATIONS

T.V. Karstang et al.: "Infrared Spectroscopy and Multivariate calibration used in Quantitative analysis of additives in high–density polyethylene" Chemometrics and Intelligent Laboratory Systems, vol. 14, No. 1–3, Apr. 1992, pp. 331–339, XP000274890.

R. Feldhoff et al.: "On–Line Post Consumer Package Identification by Nir Spectroscopy Combined with a Fuzzyartmap Classifier in an Industrial Environment" Applied Spectroscopy., vol. 51, No. 3, 1997, pp. 362–368, XP000698673.

\* cited by examiner

*Primary Examiner*—Constantine Hannaher
*Assistant Examiner*—Timothy Moran
(74) *Attorney, Agent, or Firm*—Frommer Lawrence & Haug LLP; William S. Frommer; Samuel H. Megerditchian

(57) ABSTRACT

The present invention relates to a method for identification of plastic materials of interest by optical measurements, preferably spectroscopic measurements, comprising the steps of measuring a sample and providing a sample spectrum, providing reference spectra for a given group of reference materials of interest, determining spectral distances between sample spectrum and reference spectra, material identification by associating the sample to the material having the reference spectrum with the smallest spectral distance to the sample spectrum. In this method at least one identification frequency range having a high absolute deviation ratio D and/or a high smoothed deviation ratio D' between all pairs of possible plastic materials of interest is determined, and that said spectral distance is only determined within said at least one identification frequency range.

30 Claims, 3 Drawing Sheets

Figure 1:
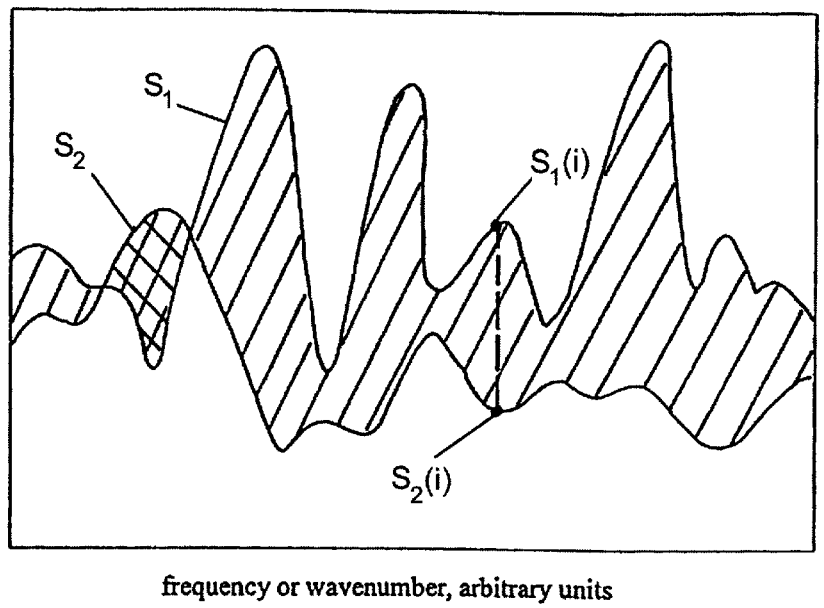

METHOD AND APPARATUS FOR IDENTIFICATION OF PLASTIC MATERIALS BY OPTICAL MEASUREMENTS

FIELD OF THE INVENTION

The present invention relates to a method and an apparatus for identification of different plastic materials by optical measurements, especially by spectroscopy analysis.

BACKGROUND OF THE INVENTION

The plastics industry has experienced global growth in the past decades and this tendency will be continued in the future, as plastic products are used for a lot of products, being sold in increasing numbers. Especially casings for computers, laptops, screens, televisions, packaging materials, interior elements and devices in cars as well as external automotive parts, furniture, casings for electronic devices, etc. are manufactured from different plastic materials or even combinations thereof.

With the increasing manufacturing of plastic and plastic products, disposal and recycling of such plastic products have become a problem for the environment. Therefore, it is desired to recycle most of the plastic materials. For an effective recycling it is necessary that these plastic materials are identified and separated, as different materials require different and separated further treatments.

As sorting and identification techniques, different methods are known in the art, using e.g. properties such as density, electrical, magnetical, tripological or chemical separation. But, there are similar polymers, like co-polymers or polymer blends, as well as materials with different additives that cannot be separated by these methods.

Therefore, optical measurements, especially spectroscopic techniques have been developed. Different techniques are known in the art, as e.g. Near Infrared Reflection (NIR), Mid-Infrared Reflection (MIR), MIR Pyrolysis, MIR Acousto-Optic Tunable Filters (AOTF), RAMAN Scattering, or others. Among the above mentioned techniques, NIR, MIR and RAMAN are the techniques with the best reliability for identification of plastic materials, as used in modern products.

With the above mentioned or other spectroscopic measurements, samples are measured and sample spectra as well as reference spectra for specific plastic materials are provided. Normally, the raw data, achieved by the spectroscopic measurement, are further prepared and/or processed, e.g. by performing a Fourier Transformation, a base line correction, a vector normalization, etc., in order to make a further comparison of reference spectra and sample spectra easier and more reliable. These preparations of raw data can be performed e.g. by means of a computer together with respective computer programs.

After a sample spectrum has been measured and prepared or processed, it will be compared to reference data of all plastic materials of interest. Spectral distances between the sample spectrum and between each reference spectrum is determined, whereas the sample is supposed to be of the material with the reference spectrum that shows the minimum spectral distance, ideally the spectral distance is equal to 0.

Because the number of plastic materials of interest is possibly very large, a lot of comparing steps of the sample spectra with each reference spectra over the whole frequency range, e.g. in MIR between 400 and 4000 $cm^{-1}$, is necessary. Such a procedure is very time consuming, and the correct identification ratio is unsufficiently low, as the measured and achieved spectral distances do not clearly distinguish for some possible materials of interest.

OBJECTS AND SUMMARY OF THE INVENTION

It is therefore an object of the present invention to provide a method and an apparatus for identification of plastic materials of interest, wherein the procedure can be conducted in a less time consuming way and wherein more reliable results and therefore a higher correct identification rate can be achieved.

This object is solved by a method according to claim 1 and an apparatus according to claim 24. Claims 2 to 23 show preferred features of the inventive method of independent claim 1 and claims 25 to 26 show preferred embodiments of the apparatus according to claim 24.

DETAILED DESCRIPTION OF THE INVENTION

According to the invention, at least one identification range having a high absolute deviation ratio D and/or a high smoothed deviation ratio D' between all pairs of possible plastic materials of interest is determined and a spectral distance, i.e. the added distance between two spectra to be compared over the relevant region, is only determined within said at least one identification ratio. A "high" ratio in this sense covers both high plus and minus values.

The absolute deviation ratio reflects a ratio between the absolute signal distances of the spectra of two materials to be compared and the consistency or noise and is therefore an indicator for the reliability of the measurement at the respective frequency for these materials. The identification frequency ranges are therefore those areas, where the distance between the absolute signals of the respective spectra to be compared is very high on the one hand and the noise is very low on the other hand, thereby leading to a high reliability. The noise may be measured by means of a standard deviation, when measuring a certain number of samples with the same molecular origin, but also any other value for the noise or consistency of the measurements can be used.

With the inventive method, only the frequency ranges, where spectral differences are present, will be investigated. Thereby a processing of areas, where the still remaining possible plastic materials of interest do not show remarkable or measurable differences, is omitted, thereby saving valuable measurement time.

Furthermore, and even more important, the reliability of a measurement results can be increased by comparing spectra only within limited ranges, as measurement noise will add up over a wide measurement range and may probably eliminate signal or spectra differences, making an identification impossible. Further, spectral distances that can be measured in a certain frequency range may add up to 0 with spectral distances in another frequency range, when measuring over the whole possible range, i.e. over more than the identification frequency range, as it is done according to the known methods of the state of art. The method according to the invention therefore avoids erroneous identification decisions.

The method according to the present invention has especially advantages, when polymers, containing additives, and similar plastic materials, having similar spectra over a wide frequency range, have to be identified.

It has been shown that with the present invention a reliability, i.e. a correct identification rate, of over 95 to 98% can be achieved within less than 2 seconds when identifying the standard main stream plastics.

Depending on the materials that have to be identified and separated, the reliability factor of the identification results is therefore up to 3 times better in comparison with a method according to the state of art.

When determining more than one identification frequency range and simply adding the spectral differences in all identification frequency ranges, it should be cross checked that there is no nullification or remarkable decreasing of the overall spectral difference (and therefore of the sum or integral of the deviation ratio over all identification frequency ranges) between all pairs of possible materials, as this might decrease measurement reliability. No problems will arise, when each identification frequency range is first considered separately and the overall spectral difference over all frequency ranges is determined by adding only absolute values |x|, i.e. positive values, of each identification frequency range, as spectral differences in each identification range can then only add up, when not taking into account different signs (plus/minus).

According to another aspect of the present invention, the method comprises at least two process or method levels, being conducted subsequently, wherein in each level the number of possible materials of interest is further limited. Within each level, the sample spectra, achieved by optical measurement, are only provided within a limited identification frequency range. This can either be achieved by measuring the samples only in these identification ranges in each level or by measuring the samples only once over a complete measurement range and further only providing the respective interesting frequency range for each level, what is the more preferred way.

The identification frequency ranges are determined in dependence of the group of plastic materials of interest in each level. The sample spectrum is compared with respective reference spectra only within these limited identification frequency ranges and the spectral distance is then determined, again only within these limited identification frequency ranges. Then at least two materials in the first level, at least one material in all levels starting with the second level and only one material in the last level for final identification having reference spectra with the smallest spectral distance is or are chosen. Thereby, a number of possible materials will be limited step by step until the final identification of the sample material in the last measurement or procedure level.

Such a procedure is especially useful, as some groups of plastic materials can easily be distinguished in the early levels, because they have clearly different spectra in certain identification frequency ranges. In the first levels, the number of possible materials is therefore very fast limited to a group of materials showing similar spectra.

Within the groups of materials with similar spectra, again, only the frequency ranges where spectral differences are present, will be investigated and measured, saving valuable measurement time and increasing reliability as explained above.

With a given group of materials of interest, it is preferable to separate specific sub-groups of materials and therefore provide a "clustering" of sub-groups within one or more process levels, in order to provide better spectra differences for all materials in each sub-group and therefore have higher deviation ratios. Identification frequency ranges can then better be adapted for these limited number of materials in each sub-group, decreasing measurement time and increasing reliability.

Such a clustering can e.g. realize sub-groups with materials "easy" to identify from each other and sub-groups containing materials "difficult" to identify from each other. A criterion therefore can again be the deviation ratio between two materials. E.g. materials having a normalized deviation ratio over 2 or under −2 being considered as easy to identify and therefore being in a first sub-group, and materials having a normalized deviation ratio between 1 and 2 or −1 and −2 respectively being difficult in identification and forming a second sub-group.

The inventive method therefore succeeds in the first levels in limiting the number of possible plastic materials of interest, thereby allowing especially in the further levels a specific determination and limitation of the identification frequency range, highly increasing the reliability and also decreasing the process time, in a comparison with the state of art.

It should be noticed at this point that it might also be possible that a material, showing a clearly distinctive spectrum in comparison to all other possible materials, can be identified directly after the first level.

The present invention has a special importance when identifying plastic materials that are used in modern products, as e.g. the group comprising ABS (Acrylnitril-Butadien-Styrol), HIPS (High Impact Polysterene), SAN (Styrene Acrylnitrile), PP (Polypropylene), PE (Polyethylene), PA (Polyamide), POM (Polyoxymethylene), PMMA (Polymethyl-Methacrylate), PC (Polycarbonate), PPO (Polyphenyloxide), combinations of PC and ABS, combinations of HIPS and PPO. These materials can be provided as essentially pure materials or they can comprise additives, especially hazardous additives like flame retardants, e.g. halogenated or phosphated flame retardants.

For a recycling process or for any other preparation of the materials, it is very important to know and to identify, which additives are comprised in a plastic material. As the spectra of the plastic materials comprising different additives do not show a clear spectral distance over the whole frequency range, the reliability or correct identification rate especially of these materials is much better with the inventive method in comparison with the known methods of the art.

It is especially preferred that the absolute deviation ratio D (X, Y, f), wherein X, Y are two of the possible plastic materials of interest, is determined by measuring a number N of different samples of the same molecular origin X, Y, numerically subtracting the N-weighted average of the measured signal S of the vibrational bands of sample Y from the N-weighted average of the measured signal S of the vibrational bands of sample X and normalizing by a term of the standard deviations or another value for the noise R of the sample X and Y measurements, wherein D is dependent of the measurement wavelength, the wavenumber or the frequency f.

The absolute deviation ratio is therefore determined according to the following formula:

$$D(X, Y, f) = \frac{[S(X, N, f) - S(Y, N, f)]}{[R(X, N, f) + R(Y, N, f)]}$$

It is further possible to determine an integral deviation ratio D' (X, Y, f) wherein this integral deviation ratio is the average value of the absolute deviation ration D (X, Y, f)

within a wavenumber or frequency range of f−Δf and f+Δf. Δf is normally smaller than 40 cm$^{-1}$, preferably smaller than 20 cm$^{-1}$, further preferably smaller than 10 cm$^{-1}$. Thereby a smoothing over 2 or 4 measurement points is achieved, depending on the measurement resolution.

According to a preferred embodiment of the present invention, the identification frequency ranges only comprise wavenumbers or frequencies, for which either the normalized value of the absolute deviation ratio D or the smoothed deviation ratio D' is higher than 1 or lower than −1, for all pairs of possible materials of interest.

When using the absolute deviation ratio D for the determination of identification frequency ranges, possibly a lot of interrupted or small frequency ranges will occur, whereas when using the smoothed deviation ratio D', the respective graph of deviation ratio will be smoother, thereby leading to wider frequency ranges. Using the absolute deviation ratio will lead to still more accurate results, whereas using the smoothed deviation ratio will simplify the measurement or the controlling of the respective measurement devices.

According to the above described method, the identification frequency ranges as stated in claims 12 to 21 have been determined and proven to be useful with the respective group of possible plastic materials of interest.

As the materials of interest may vary depending on the application, e.g. depending on the company using the inventive method or the inventive apparatus and/or on the products to be recycled, it will be obvious to an artisan from the above explanation that combinations of process structures having different levels can be provided, in order to fit the inventive method to the desired application. Thereby different matrixes, i.e. different process levels with different identification frequency ranges can be combined to form a desired multi-level measurement matrix, being in accordance with the present invention.

One of the preferred measurement matrixes has in the first level an identification frequency range IFR$_1$, measuring from 600 to 750 cm$^{-1}$, 850 to 1200 cm$^{-1}$, 1350 to 1500 cm$^{-1}$, 2750 to 3000 cm$^{-1}$ and an intermediate frequency range IFR$_2$ measuring from 850 to 1100 cm$^{-1}$, 2150 to 2300 cm$^{-1}$ and 3000 to 3120 cm$^{-1}$. In the second level, an intermediate frequency range IFR$_3$ measuring from 650 to 1800 cm$^{-1}$, 2150 to 2300 cm$^{-1}$ and 2750 to 3150 cm$^{-1}$, and an identification frequency range IFR$^4$, measuring from 800 to 1440 cm$^{-1}$, 1470 to 1480 cm$^{-1}$, 1520 to 1570 cm$^{-1}$ and 1650 to 1750 cm$^{-1}$, will be used.

Depending on the results after the second level, a third level may be added, having a identification frequency range IFR$_5$, from 650 to 1800 cm$^{-1}$ and 2750 to 3150 cm$^{-1}$, or an identification frequency range IFR$_6$, from 850 to 1100 cm$^{-1}$, 1400 to 1800 cm$^{-1}$ and 3100 to 3300 cm$^{-1}$. This structure is especially useful and shows highly reliable identification rates when identifying ABS, HIPS, SAN with halogenated or phosphates flame retardants and PC+ ABS blends or HIPS+PPO blends.

This third level can be also directly integrated into the above described second level, forming only a 2-level measurement.

The invention also relates to an inventive apparatus, comprising a measurement device, measuring a sample and giving a sample spectrum, a first storage means, storing said sample spectrum and reference spectra for the possible materials, means providing sample spectrum and reference spectra only in at least one identification frequency range, a second storage means, storing and providing said sample and reference spectra only in said at least one identification frequency range, means, determining spectral distances between said sample spectrum and said reference spectra in the respective at least one identification frequency range, and means, associating the sample to at least one material having the reference spectrum or spectra with the smallest spectral distance to the sample spectrum.

The above mentioned first and second storage means can of course physically be the same means, not only separated means.

Such an apparatus is especially useful in operating a method as described above in a very efficient way and the advantages of the inventive method and the preferred procedures can be directly utilized by this apparatus.

In a preferred embodiment, the apparatus further comprises storage means storing multiple spectra of each of at least two materials and means determining an absolute deviation ratio D and/or an smoothed deviation ratio D' of groups of each two of the materials of interest.

It is advantageous that the apparatus further comprises means comparing said deviation ratios D and/or D' and determining at least one identification frequency range, for which the normalized value of the absolute deviation ratio D and/or of the smoothed deviation ratio D' is higher than 1 or lower than −1 for all pairs of possible materials of interest.

With these features of the apparatus, an integral apparatus, being able to conduct all operations for achieving a high identification rate without additional external means, is provided, realizing a powerful tool for identification of plastic material, being difficult to identify with apparatuses according to the state of art.

Figure 2:
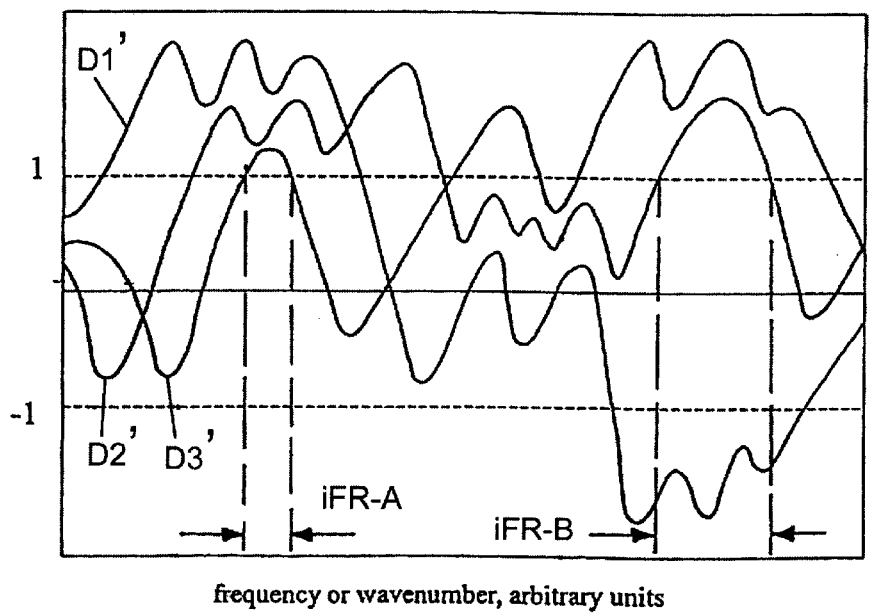
Figure 3:
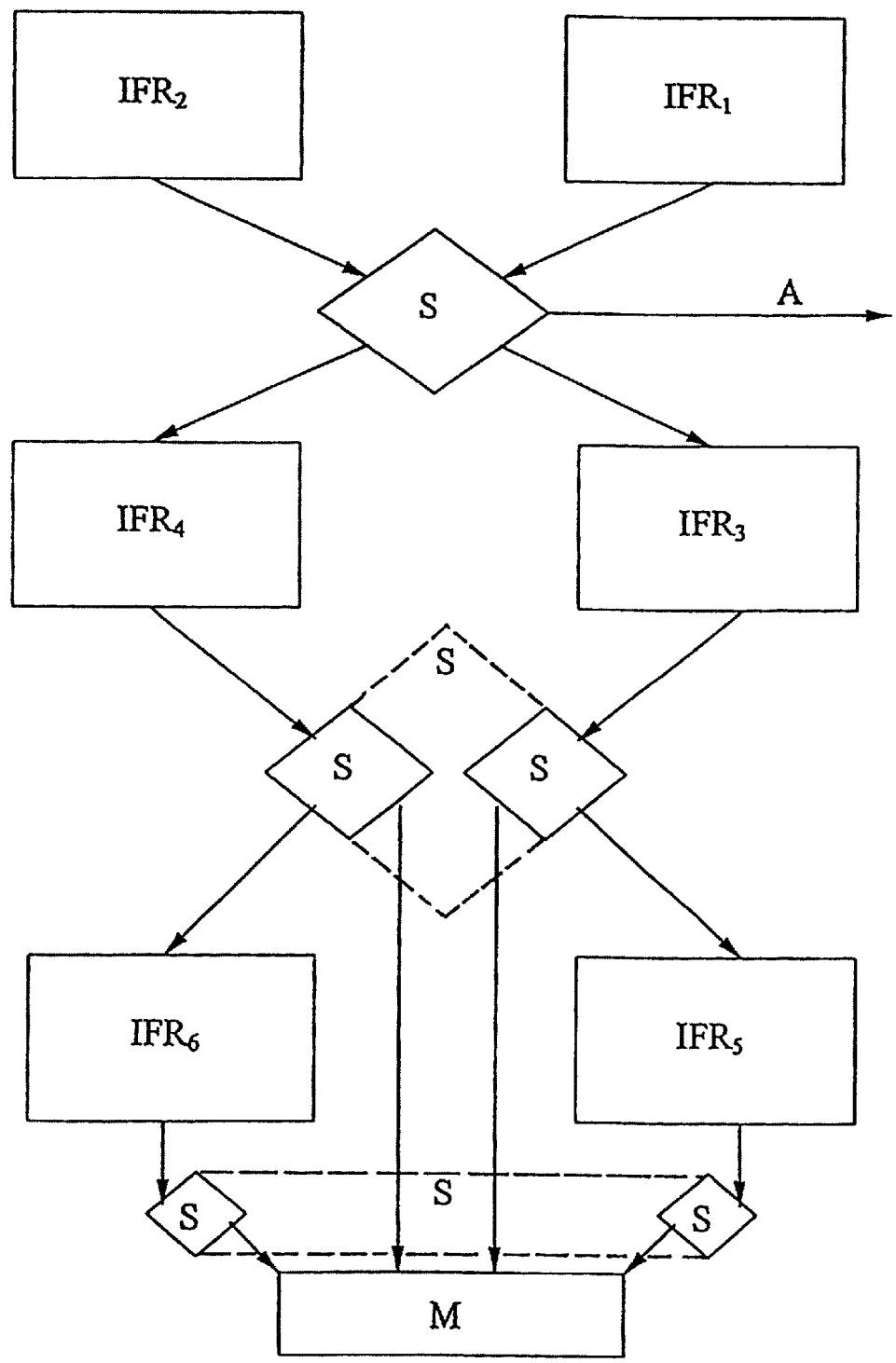

Further features of the invention will be apparent from the description in connection with the attached drawings, wherein FIG. 1 schematically shows a simplified graph of two spectra for determining the spectral distance, FIG. 2 schematically shows a simplified graph of an smoothed deviation ratio for two materials of interest for determining an identification frequency range, and FIG. 3 schematically shows a diagram of a part of a preferred process structure.

Figure 4:
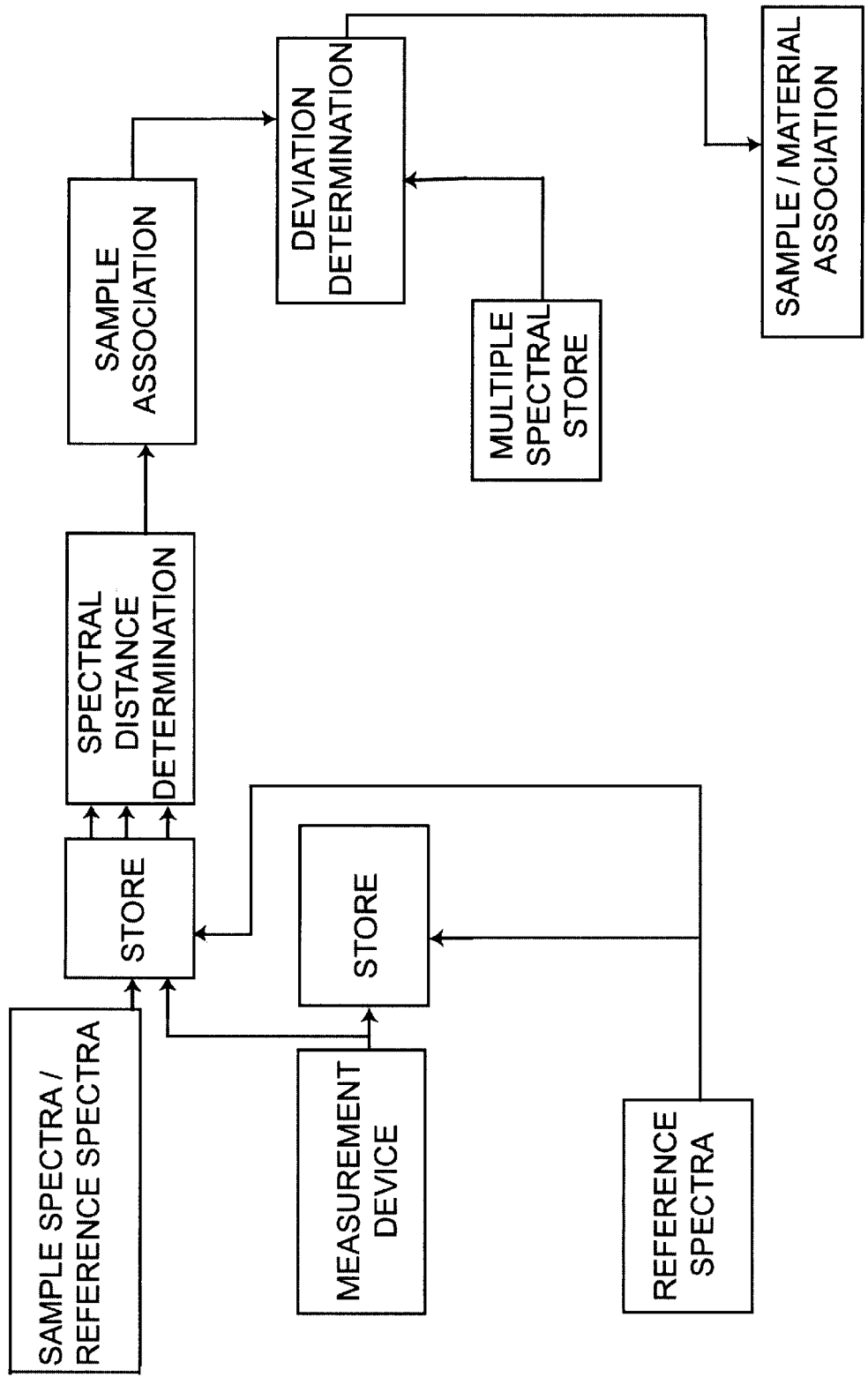

FIG. 4 is a schematic diagram of an embodiment of an apparatus according to the present invention.

FIG. 1 shows two graphs S1 and S2, indicating a signal intensity S (y-axis) depending on the frequency or the wavenumber (x-axis). When determining the spectral distance SD between the two spectra S1 and S2, the intensity of signal S2 is subtracted from the intensity of signal S1 at a certain frequency or wavenumber i, and the difference between the signals S1(i) and S2(i) are summarized over the whole wavenumber range, according to the following formula:

$$SD=\Sigma S1(i)-S2(i)$$

This method is called "principle least square method" (PLS) and uses the Euclidean distances.

As can be seen in FIG. 1, the difference between the signals can have both positive and negative sign or value, thereby possibly eliminating the noticeable difference between the spectra, when comparing over the complete range, let alone irregularities caused by measurement noise.

Further methods, like PCA (Principle Component Analysis), PDA (Principal Discriminant Analysis), or more complex methods, based on PCA for data reduction and factor analysis, like "Neural Networks" and "Mahalanobis Distances", can of course be used within the scope of the inventive method, but do not necessarily show better results than the relative simple PLS method.

FIG. 2 shows schematically three graphs D1' (X, Y), D2' (X, Z) and D3' (Y, Z), representing the smoothed deviation ratio between each two of three possible materials of interest X, Y, Z over a certain frequency range or wavenumber range. As can be seen, the smoothed deviation ratios D1' to D3' have some frequency ranges, where the normalized value is larger than 1 or lower than −1. These areas characterize a high ratio of signal distances to noise of the two respective materials of interest. The identification frequency range for the materials X, Y, Z are determined by choosing a frequency or wavenumber range, where for all graphs D1', D2' and D3' the normalized value is above 1 or below −1. Here two identification frequency ranges IFR-A and IFR-B are identified, but it is also possible that only one or also more distinct identification frequency ranges will be found.

FIG. 3 schematically shows a diagram representing a part of a possible measurement structure of 3 levels, wherein, depending on the results of the second level, the third level may be omitted. In the first level, an identification frequency range $IFR_1$ (600 to 750 $cm^{-1}$, 850 to 1200 $cm^{-1}$, 1350 to 1500 $cm^{-1}$, 2750 to 3000 $cm^{-1}$) and an identification frequency range $IFR_2$ (850 to 1100 $cm^{-1}$, 2150 to 2300 $cm^{-1}$, 3000 to 3120 $cm^{-1}$) will be taken into account. Such a first level will be especially used when the plastic materials of interest comprise ABS, HIPS, SAN, together with other materials as PP, PE, POM.

FIG. 4 schematically represents an apparatus for identifying at least one plastic material in a sample comprising said at least one plastic material by optical measurement. As seen in FIG. 4, the apparatus has a measurement device for measuring said sample and giving a sample spectrum; first storage means for storing said sample spectrum and a reference spectra; means for providing sample spectrum and reference spectra only in at least one identification frequency range; second storage means for storing and providing said sample and reference spectra only in said at least one identification frequency range; means for determining spectral distances between said sample spectrum and said reference spectra in respective identification frequency ranges; means for associating the sample to at least one material having the reference spectrum or spectra with the smallest spectral distance to the sample spectrum; third storage means for storing multiple spectra of each of at least two plastic materials; means for determining an absolute deviation ratio D and/or smoothed deviation ratio D' of groups of said plastic materials; and means for associating the sample to at least two materials in a first level, to at least one material in all levels starting with a second level, and to only one material in a last level, having the reference spectrum or spectra with the smallest spectral distance to the sample spectrum.

After comparing the sample spectra and the respective reference spectra within the identification frequency range, as explained above, it is known, whether the unknown sample is of the group consisting of ABS, HIPS, SAN, or the group consisting of PP, PE, or POM. The step of comparing and selection is always shown in the diagram as S, although not representing a distinct level.

In this case, it is found that the unknown sample comprises ABS, HIPS or SAN, in the second level, the identification frequency range $IFR_4$ (800 to 1440 $cm^{-1}$, 1470 to 1480 $cm^{-1}$, 1520 to 1570 $cm^{-1}$ and 1650 to 1750 $cm^{-1}$) will be taken into account. Within this frequency range, materials with halogenated flame retardants can be clearly distinguished. In this case, the sample does not contain halogenated additives, a frequency range $IFR_6$ (850 to 1100 $cm^{-1}$, 1400 to 1800 $cm^{-1}$ and 3100 to 3300 $cm^{-1}$) will be taken into account in a third level of measurement.

In case, the first level of measurement shows that the unknown sample comprises a PC-ABS blend, the identification frequency range $IFR_3$ (650 to 1800 $cm^{-1}$, 2150 to 2300 $cm^{-1}$ and 2750 to 3150 $cm^{-1}$) will be taken into account in a second level of measurement. Should the sample consist of HIPS-PPO blend for different blending ratios, a third level of measurement will be conducted over an identification frequency range $IFR_5$ (650 to 1800 $cm^{-1}$ and 2750 to 3150 $cm^{-1}$).

It is also possible to combine the respective second and third levels and to take into account either $IFR_4$ and $IFR_6$ or $IFR_3$ and $IFR_5$ together in the second level, wherein the third level is omitted. This realizes a pure 2-level measurement or a 2-level matrix for the identification of the plastic materials.

In case, the first level of measurement shows that the unknown sample is of the group consisting e.g. of PP, PE, POM, similar further levels are entered with respective identification frequency ranges. This structure is only indicated by an arrow A and not shown in detail in FIG. 3, in order not to make the structure too complicated, but only to show an example of an inventive structure. Multiple further structures can be formed by the artisan using the teaching of this invention.

After 2 or 3 levels of frequencies, limiting step by step the possibilities for the material of the sample, a final result M, indicating the material of the sample, will be achieved with a high accuracy, here with over 98% correct identification rate. Only for completion, it is noticed that the steps of comparison S can be combined for each horizontal level, i.e. not only in the first level but also in further levels (indicated by dashed lines).

It will be apparent that any other combination of identification of frequency ranges within the measurement structure, especially any combination of the above disclosed identification frequency ranges for the specific materials, can be combined by the artisan, without deviating from the scope of the present invention.

The features of the present invention disclosed in the specification, the claims, and/or in the accompanying drawings may, both separately and in any combination thereof, be material for realizing the invention in various forms thereof.

What is claimed is:

1. A method for identifying at least one plastic material in a sample comprising said at least one plastic material by optical measurement, comprising the steps of:

measuring said sample and providing a sample spectrum;

providing reference spectra for a group of reference materials;

determining at least one identification frequency range, said range comprised of a high absolute deviation ratio D and/or a high smoothed deviation ratio D', determining spectral distances between said sample spectrum and said reference spectra within said identification frequency range;

identifying said plastic material by comparing the sample spectrum to the reference spectrum, providing a sample spectrum only in at least one identification frequency range in a number of levels, wherein said at least one identification frequency range in each level is different from the identification frequency range in the preceding level;

providing reference spectra in respective identification frequency ranges for the possible materials in the respective levels;

determining spectral distances between sample spectrum and reference spectra only in the respective identification frequency ranges; and associating the sample to at least two materials in the first level, to at least one material in all levels starting with the second level, and to only one material in a last level, having the reference spectrum or spectra with the smallest spectral distance to the sample spectrum.

2. The method according to claim 1, wherein said plastic material is selected from the group consisting of ABS (Acrylnitril-Butadien-Styrol), HIPS (High Impact Polysterene), SAN (Styrene-Acrylnitrile), PP (Polypropylene), PE (Polyethylene), PA (Polyamide), POM (Polyoxymethylene), PMMA (Polymethyl-Methacrylate), PC (Polycarbonate), PPO (Polyphenyloxide), PA6, PA12, PA66, PBT, PET and combinations thereof.

3. The method according to claim 2, wherein the identification frequency range for PP, PE, POM is 650 to 750 $cm^{-1}$, 850 to 1200 $cm^{-1}$, 1350 to 1500 $cm^{-1}$, and 2750 to 3000 $cm^{-1}$.

4. The method according to claim 2, wherein the identification frequency range for HIPS, ABS, SAN is 850 to 1100 $cm^{-1}$, 2150 to 2300 $cm^{-1}$ and 3000 to 3120 $cm^{-1}$.

5. The method according to claim 2, wherein the identification frequency range for PA6, PA12, PA66 is 1090 to 1350 $cm^{-1}$.

6. The method according to claim 2, wherein the identification frequency range for PBT and PET is 1320 to 1440 $cm^{-1}$.

7. The method according to claim 2, wherein said PP comprises halogenated flame retardants, and wherein the identification frequency range is 550 to 1360 $cm^{-1}$ and 1500 to 1800 $cm^{-1}$.

8. The method according to claim 2, wherein said PC comprises halogenated flame retardants, and wherein the identification frequency range is 550 to 1800 $cm^{-1}$.

9. The method according to claim 2, wherein said HIPS, ABS, SAN comprise halogenated flame retardants, and wherein said identification frequency range is 800 to 1440 $cm^{-1}$, 1470 to 1480 $cm^{-1}$, 1520 to 1570 $cm^{-1}$ and 1650 to 1750 $cm^{-1}$.

10. The method according to claim 2, wherein said HIPS, ABS, SAN comprise phosphated flame retardants, and wherein said identification frequency range is 850 to 1100 $cm^{-1}$, 1400 to 1800 $cm^{-1}$ and 3100 to 3300 $cm^{-1}$.

11. The method according to claim 2, wherein the identification frequency range of a sample comprising the combination of PC and ABS is 650 to 1800 $cm^{-1}$, 2150 to 2300 $cm^{-1}$ and 2750 to 3150 $cm^{-1}$.

12. The method according to claim 2, wherein the identification frequency range of a sample comprising the combination HIPS and PPO is 650 to 1800 $cm^{-1}$ and 2750 to 3150 $cm^{-1}$.

13. The method according to claim 2, wherein said combination is PC and ABS or HIPS and PPO.

14. The method according to claim 1, wherein said at least one plastic material is substantially pure.

15. The method according to claim 1, wherein said at least one plastic material comprises additives.

16. The method according to claim 15, wherein said additive is a hazardous additive.

17. The method according to claim 15, wherein said additive is a flame retardant.

18. The method according to claim 15, wherein said at least one plastic material comprises phosphate or compounds therefrom.

19. The method according to claim 1, wherein said absolute deviation ratio is represented by D (X, Y, f), wherein XY is one pair of a group of plastic materials determined by measuring a number N of different samples of a same molecular origin XY, numerically subtracting a N-weighted average of a measured signal of vibrational bands of sample Y from a N-weighted average of a measured signal of vibrational bands of sample X and normalizing by standard deviations R for the measurements of samples X and Y, wherein D is dependent on the measurement wavenumber or frequency f.

20. The method according to claim 1, wherein said smoothed deviation ratio is represented by D' (X, Y, f), wherein D' (X, Y, f) is an average of D (X, Y, f) within a wavenumber or frequency range of f−Δf and f+Δf.

21. The method according to claim 20, wherein Δf is less than 40 $cm^{-1}$.

22. The method according to claim 20, wherein Δf is less than 20 $cm^{-1}$.

23. The method according to claim 20, wherein Δf is less than 10 $cm^{-1}$.

24. The method according to claim 1, wherein the identification frequency range comprises wavenumbers or frequencies, wherein a normalized value of the absolute deviation ratio D or of the smoothed deviation ratio D' is higher than 1 or lower than −1.

25. The method according to claim 1, wherein in a first process level the identification frequency ranges are 600 to 750 $cm^{-1}$, 850 to 1200 $cm^{-1}$, 1350 to 1500 $cm^{-1}$, 2750 to 3000 $cm^{-1}$ ($IFR_1$), 850 to 1100 $cm^{-1}$, 2150 to 2300 $cm^{-1}$ and 3000 to 3120 $cm^{-1}$ ($IFR_2$), and the identification frequency ranges in a second process level are 650 to 1800 $cm^{-1}$, 2150 to 2300 $cm^{-1}$, 2750 to 3150 $cm^{-1}$ ($IFR_3$), 800 to 1440 $cm^{-1}$, 1470 to 1480 $cm^{-1}$, 1520 to 1570 $cm^{-1}$ and 1650 to 1750 $cm^{-1}$ ($IFR_4$).

26. The method according to claim 25, wherein said second process level further comprises the identification frequency range 650 to 1800 $cm^{-1}$, 2750 to 3150 $cm^{-1}$ ($IFR_5$) 850 to 1100 $cm^{-1}$, 1400 to 1800 $cm^{-1}$ and 3100 to 3300 $cm^{-1}$ ($IFR_6$).

27. The method according to claim 1, wherein said optical measurement is spectroscopic.

28. The method according to claim 27, wherein said flame retardant is halogenated.

29. An apparatus for identifying at least one plastic material in a sample comprising said at least one plastic material by optical measurement, comprising:

a measurement device for measuring said sample and giving a sample spectrum;

first storage means for storing said sample spectrum and a reference spectra;

means for providing sample spectrum and reference spectra only in at least one identification frequency range in respective levels, wherein said at least one identification frequency range in a respective level is different from the identification frequency range in a preceding level;

second storage means for storing and providing said sample and reference spectra only in said at least one identification frequency range;

means for determining spectral distances between said sample spectrum and said reference spectra in respective identification frequency ranges;

means for associating the sample to at least one material having the reference spectrum or spectra with the smallest spectral distance to the sample spectrum;

third storage means for storing multiple spectra of each of at least two plastic materials;

means for determining an absolute deviation ratio D and/or smoothed deviation ratio D' of groups of said plastic materials; and means for associating the sample to at least two materials in a first level, to at least one material in all levels starting with a second level, and to only one material in a last level, having the reference spectrum or spectra with the smallest spectral distance to the sample spectrum.

30. The apparatus according to claim 29, further comprising means for comparing said deviation ratios D and/or D' of a group of said plastic material and determining at least one identification frequency range, wherein a normalized value of the absolute deviation ratio D and/or the smoothed deviation ratio D' is higher than 1 or lower than −1.

* * * * *